United States Patent [19]

Sugihara et al.

[11] Patent Number: 4,558,068
[45] Date of Patent: Dec. 10, 1985

[54] SPIROBENZOFURANONES AND THEIR USE IN TREATING PEPTIC ULCERS

[75] Inventors: Hirosada Sugihara, Osaka; Masazumi Watanabe, Kawanishi; Mitsuru Kawada, Hyogo; Isuke Imada, Osaka, all of Japan

[73] Assignee: Takeda Chemical Industries, Ltd., Osaka, Japan

[21] Appl. No.: 630,291

[22] Filed: Jul. 12, 1984

[30] Foreign Application Priority Data

Aug. 1, 1983 [JP] Japan ................................ 58-141704

[51] Int. Cl.$^4$ ..................... A61K 31/34; C07D 307/94
[52] U.S. Cl. ..................................... 514/462; 549/345
[58] Field of Search .......................... 549/345; 514/462

[56] References Cited

U.S. PATENT DOCUMENTS 4,284,644  8/1981  Sugihara et al. ..................... 514/462
4,330,554  5/1982  Sugihara et al. ..................... 514/462
4,342,779  8/1982  Sugihara et al. ..................... 514/462

Primary Examiner—Henry R. Jiles
Assistant Examiner—Bernard I. Dentz
Attorney, Agent, or Firm—Wegner & Bretschneider

[57] ABSTRACT

Novel spirobenzofuranone compounds of the formula:

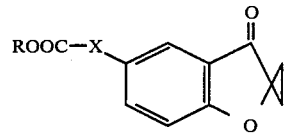

wherein R is a hydrogen atom or a lower alkyl and —X— is

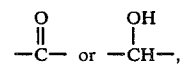

and a pharmaceutically acceptable salt thereof, have gastric secretion inhibitive, antiulcer activities, and are of value as drugs.

7 Claims, No Drawings

SPIROBENZOFURANONES AND THEIR USE IN TREATING PEPTIC ULCERS

This invention relates to novel spirobenzofuranone compounds which are of value as medicines, and methods for producing said compounds.

More particularly, this invention relates to a novel spirobenzofuranone compound of the formula:

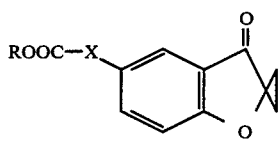
(I)

wherein R is a hydrogen atom or a lower alkyl and —X— is

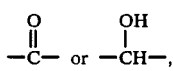

and a pharmaceutically acceptable salt thereof, and its production.

Referring to the above formula (I), R is a hydrogen atom or a straight-chain or branched lower alkyl group of 1 to 5 carbon atoms, such as methyl, ethyl, n-propyl, n-butyl, isopropyl, tert-butyl or n-pentyl.

The spirobenzofuranone compound of the formula (I) wherein R is a lower alkyl and —X— is

can be produced, for example, from the compound (II) described in Sugihara et al., U.S. Pat. No. 4,284,644 granted Aug. 18, 1981 in the following manner.

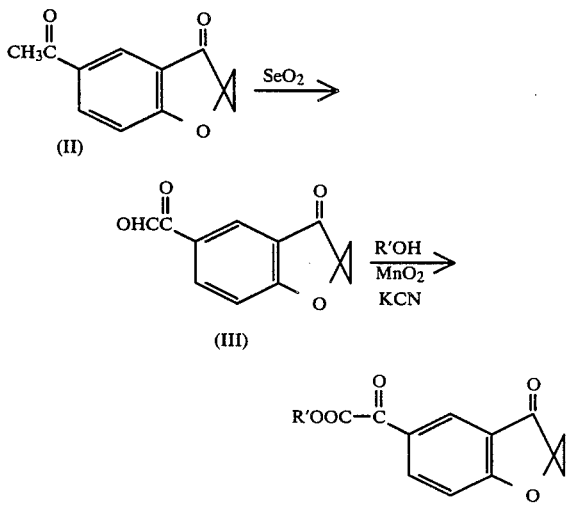

In the above reaction formula, R' is a lower $C_{1-5}$ alkyl group. Reacting the compound (II) with selenium dioxide or the like in a mixed solvent such as dioxane-water under reflux conditions gives rise to the α-ketoaldehyde (III). This α-ketoaldehyde may, with or without purification, be subjected to the next reaction. Thus, the compound (III) is oxidized with, for example, manganese dioxide in a suitable alcoholic solvent (R'OH) in the presence of a catalyst such as sodium cyanide, potassium cyanide, etc., whereby the contemplated spiro compound, i.e. α-ketoester is produced.

Referring, further, to the formula (I), the compound (I) wherein R is a lower alkyl and —X— is

i.e. α-hydroxyester can be produced by reducing the α-ketoester of the formula:

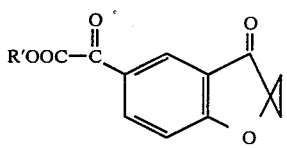

wherein R' is as defined hereinbefore.

The compound of the formula (I) wherein —X— is

and R is a hydrogen atom, i.e. α-hydroxyacid can be produced by hydrolyzing the α-hydroxyester of the formula

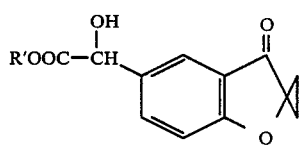

wherein R' is as defined hereinbefore which is obtainable by the above-mentioned reduction of the α-ketoester of the formula:

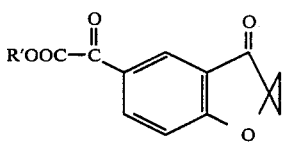

The reduction may be carried out by a method using a metal borohydride as a reducing agent or a catalytic reduction method. The reduction reaction using a metal borohydride is conducted in a suitable solvent, and while the solvent may be any solvent only if it does not interfere with the reaction, ether, tetrahydrofuran, dioxane, dimethoxyethane, methylene chloride, pyridine or isopropyl alcohol or a mixture of such solvents can be employed. As regards the reducing agent used for the above-mentioned reduction reaction, metal borohydrides such as sodium borohydride, potassium borohydride, etc. are preferred. The reaction temperature is generally about −70° C. to =40° C. and preferably about −30° C. to +20° C., although the reaction can be conducted at a still lower or a higher temperature so as to control the reaction rate and prevent the reduction of the 3-carbonyl group.

The catalytic reduction can be conducted in hydrogen gas streams using, for example, a palladium or Raney nickel catalyst in a suitable solvent such as methanol, ethanol, dioxane, methylene chloride or tetrahydrofuran or a mixture of such solvents. The hydrogen gas pressure may be atmospheric or superatmospheric, and the reaction temperature may range from about −20° C. to 100° C.

The hydrolysis reaction mentioned hereinbefore is conducted using, for example, a metal hydroxide such as sodium hydroxide, potassium hydroxide, barium hydroxide, etc. or an alkali metal carbonate such as sodium carbonate, sodium hydrogen carbonate or potassium hydrogen carbonate in a suitable solvent such as water, tetrahydrofuran, dioxane, methanol, ethanol, acetonitrile or N,N-dimethylformamide or a mixture of such solvents. The reaction temperature is generally about −10° C. to +100° C. and preferably about 30° C. to 80° C.

The spirobenzofuranone compound of the formula (I) wherein R is a hydrogen atom and —X— is

can also be produced by oxidizing the compound of the formula:

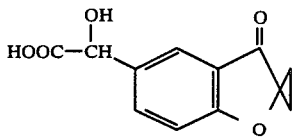

This oxidation reaction is carried out in a suitable solvent such as acetone, methylene chloride, dioxane, tetrahydrofuran or acetonitrile or a mixture of such solvents. The oxidizing agent may for example be chromic acid, chromium trioxide-sulfuric acid (Jones' reagent) or active manganese dioxide. The reaction temperature may range from about −20° C. to +50° C.

The desired compound (I) produced in the above manner can be isolated and purified by the conventional procedures (such as recrystallization, distillation, chromatography, etc.) from the reaction mixture. The compound (I) may exist in the form of optical isomers due to the presence of an asymmetric carbon atom, and each such optical isomer is within the scope of the invention.

The product compound (I) may be isolated in the form of a pharmacologically acceptable salt such as salts of metals, e.g. sodium, potassium, calcium, aluminum, etc., triethylamine salt, ammonium salt, quinine salt, cinchonine salt, etc.

The spirobenzofuranone compound (I) according to this invention has gastric secretion inhibiting activity, antiulcer activity, and is of value as an antiulcer drug for the prevention and treatment of gastric and duodenal ulcers, acute and chronic cases of gastritis, etc. In a test according to the method of Robert et al. (Gastroenterology 77, 433, 1979), this spiro compound (I) was found to strongly inhibit ulcerative damage to the gastric mucosa at the dose level of 50 mg/kg and be low in toxicity. For use of the compound (I) as a drug for the above-mentioned diseases, it can be administered orally or non-orally, either as it is or as formulated with the known excipients, carriers, etc. into suitable dosage forms such as tablets, powders, capsules, injections, suppositories, etc. The dosage depends on the subject, condition, administration route, etc. but for oral administration to adult humans in the treatment of gastric or duodenal ulcer or acute or chronic gastritis, the compound (I) can be advantageously administered in a dose of about 1 to 20 mg/kg body weight, once to about 3 times a day.

The invention is illustrated by the following nonlimiting examples:

TEST EXAMPLE

Antiulcer effect

The stress ulcer inhibiting effect of the drug was investigated in rats in accordance with the water immersion method described by K. Takagi and S. Okabe, Jap. J. Pharmacol. 18, 9, 1968.

| Compound | Dosage | % Inhibition |
|---|---|---|
| HOOC—CH(OH)—[benzofuran-cyclopropane-one structure] | 50 mg/kg, i.p. | 56%** |

**: $P < 0.05$

When the above compound was once administered orally to ICR mice in a dose of 500 mg/kg, no death was found during an observation period of 7 days.

EXAMPLE 1

In a mixture of 200 ml of dioxane and 20 ml of water is dissolved 20 g of 5-acetyl[benzofuran-2(3H),1'-cyclopropan]-3-one, and 20 g of selenium dioxide is added. The mixture is refluxed for 20 hours. After cooling, the precipitate is filtered off and the filtrate is concentrated under reduced pressure. The residue is dissolved in 300 ml of methanol and 1.0 g of potassium cyanide is added followed by portionwise addition of 30 g of active manganese dioxide with stirring at room temperature. After stirring for 30 minutes, the mixture is filtered and the filtrate is concentrated under reduced pressure. The residue is dissolved in ethyl acetate, washed with water and dried over anhydrous sodium sulfate. The solvent is then distilled off under reduced pressure and the residue is purified by silica gel column chromatography [eluent:hexane-ethyl acetate (3:1)]. Recrystallization from ether-hexane gives methyl 2-oxo-2-(3-oxospiro[benzofuran-2(3H),1'-cyclopropane]-5)-acetate as colorless prisms. Yield 13 g. M.p. 57°–58° C.

Elemental analysis: Calcd. for $C_{13}H_{10}O_5$: C, 63.41; H, 4.09, Found: C, 63.63; H, 4.21.

EXAMPLE 2

In 60 ml of tetrahydrofuran is dissolved 6.0 g of methyl 2-oxo-2-(3-oxospiro[benzofuran-2(3H),1'-cyclopropane]-5)-acetate and, with stirring at −30° C. to −20° C., 300 mg of sodium borohydride is added portionwise to the solution. After stirring for 30 minutes, 10 ml of acetone is added and the mixture is stirred at room temperature for 30 minutes and then concentrated under reduced pressure. To the residue is added ethyl acetate and the mixture is serially washed with water and dilute hydrochloric acid and dried over anhydrous sodium sulfate. The solvent is then distilled off under reduced pressure and the residue is recrystallized from ethyl acetate to give methyl 2-hydroxy2-(3-oxospiro[- benzofuran-2-(3H),1'-cyclopropane]-5)-acetate as colorless prisms. Yield 3.2 g. M.p. 112°-113° C.

Elemental analysis: Calcd. for $C_{13}H_{12}O_5$: C, 62.90; H, 4,87, Found: C, 62.80; H, 4.82.

EXAMPLE 3

In 30 ml of methanol is dissolved 2.0 g of methyl 2-oxo-2-(3-oxospiro[benzofuran-2(3H),1'-cyclopropane]-5)-acetate, and catalytic reduction is carried out using 5% palladium-on-carbon at atmospheric temperature and pressure. The reaction is continued until the amount of hydrogen absorbed reaches one equivalent. The catalyst is then filtered off and the filtrate is concentrated under reduced pressure. The residue is recrystallized from ethyl acetate to give methyl 2-hydroxy-2-(3-oxospiro[benzofuran-2(3H),1'-cyclopropane]-5)-acetate as colorless prisms. Yield 1.6 g. M.p. 112°-113° C.

EXAMPLE 4

In a mixture of 30 ml of water, 30 ml of methanol and 60 ml of tetrahydrofuran is dissolved 3.2 g of methyl 2-hydroxy-2-(3-oxospiro[benzofuran-2(3H),1'-cyclopropan]-5)-acetate, and 3.0 g of sodium hydrogen carbonate is added. The mixture is stirred at 60° C. for 20 hours and then concentrated to 30 ml under reduced pressure and dried with ethyl acetate. The aqueous layer is acidified with 1N hydrochloric acid with ice-cooling followed by extraction with ethyl acetate. The organic layer is washed with water and dried and the solvent is distilled off under reduced pressure. The residue is recrystallized from hexane-ethyl acetate to give 2-hydroxy-2-(3-oxospiro[benzofuran-2(3H),1'-cyclopropane]-5)-acetic acid as colorless prisms. Yield 2.0 g. M.p. 138°-139° C.

Elemental analysis: Calcd. for $C_{12}H_{10}O_5$: C, 61.54; H, 4.30, Found: C, 61.37; H, 4.28.

Example of preparation ready for administration

When the compound of this invention is intended for use as an anti-ulcer drug, type of suitable preparation can be exemplified as follows.

| Tablet | |
|---|---|
| (1) 2-Hydroxy-2-(3-oxospiro[benzofuran-2(3H),1'-cyclopropane]-5)-acetic acid | 50 g |
| (2) Lactose | 50 g |
| (3) Corn-starch | 29 g |
| (4) Magnesium stearate | 1 g |
| 1000 tablets | 130 g |

(1), (2) and 17 g of corn-starch were granulated together with paste prepared from 7 g of corn-starch. To this granule were added 5 g of corn-starch and (4), and the mixture was compressed by a tabletting machine to prepare 1000 tablets of 7 mm diameter, each containing 50 mg of (1).

What is claimed is:

1. A spirobenzofuranone compound of the formula:

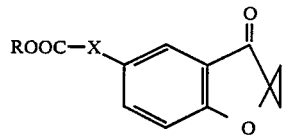

wherein R is a hydrogen atom or a lower alkyl and —X— is

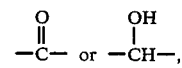

or a pharmaceutically acceptable salt thereof.

2. The compound according to claim 1, which is methyl-2-oxo-2-(3-oxospiro[benzofuran-2(3H),1'-cyclopropane]-5)-acetate.

3. The compound according to claim 1, which is methyl 2-hydroxy-2-(3-oxospiro[benzofuran-2(3H),1'-cyclopropane]-acetate.

4. The compound according to claim 1, which is 2-hydroxy-2-(3-oxospiro[benzofuran-2(3H),1'-cyclopropane]-5)-acetic acid.

5. A pharmaceutical composition for treating peptic ulcer which comprises, as an active ingredient, an effective amount of a compound or its salt as defined in claim 1, and a pharmaceutically acceptable carrier or diluent therefor.

6. A method of treating peptic ulcer, which comprises administering a compound of the formula:

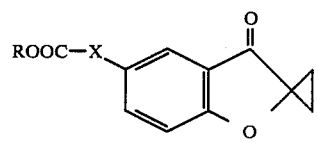

wherein R is a hydrogen atom or lower alkyl and —X— is

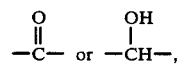

or a pharmaceutically acceptable salt thereof.

7. The method according to claim 6, wherein the compound is 2-hydroxy-2-(3-oxospiro[benzofuran-2(3H),1'-cyclopropane]-5)-acetic acid.

* * * * *